(12) United States Patent
Yasuda et al.

(10) Patent No.: US 7,335,905 B2
(45) Date of Patent: Feb. 26, 2008

(54) RADIATION IMAGE INFORMATION READING APPARATUS WITH RADIATION CONVERSION PANEL, AND METHOD OF CORRECTING SENSITIVITY OF RADIATION CONVERSION PANEL

(75) Inventors: Hiroaki Yasuda, Minamiashigara (JP); Eiichi Kanagawa, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 52 days.

(21) Appl. No.: 10/392,329

(22) Filed: Mar. 20, 2003

(65) Prior Publication Data

US 2003/0178590 A1    Sep. 25, 2003

(30) Foreign Application Priority Data

Mar. 22, 2002 (JP) ............................. 2002-080812
Mar. 4, 2003 (JP) ............................. 2003-057574

(51) Int. Cl.
G01N 23/04    (2006.01)

(52) U.S. Cl. .................... 250/587; 250/580; 250/581; 250/584; 250/585

(58) Field of Classification Search ................ 250/587, 250/580, 581, 584, 586
See application file for complete search history.

(56) References Cited

U.S. PATENT DOCUMENTS 4,734,783 A * 3/1988 Horikawa .................. 358/448
5,084,772 A * 1/1992 Shimoyama ................ 358/461
5,754,224 A * 5/1998 Kusaka ................... 348/208.12
5,760,416 A * 6/1998 Tsuchiya .................... 250/584
6,389,156 B1 * 5/2002 Tsuchino et al. ........... 382/132
6,470,065 B1 * 10/2002 Lauther ........................ 378/4
6,529,618 B1 * 3/2003 Ohara et al. ............... 382/132
6,795,572 B1 * 9/2004 Matsuno .................... 382/132
6,847,698 B2 * 1/2005 Kaifu et al. .................. 378/97

FOREIGN PATENT DOCUMENTS

| JP | 55-12429 | 1/1980 |
| JP | 63-206736 | 8/1988 |
| JP | 09-166555 | 6/1997 |
| JP | 11-258716 | 9/1999 |
| JP | 11-352300 | 12/1999 |

* cited by examiner

Primary Examiner—David Porta
Assistant Examiner—Christine Sung
(74) Attorney, Agent, or Firm—Sughrue Mion, PLLC (57) ABSTRACT

Corrective image data obtained by reading a stimulable phosphor sheet which is uniformly irradiated with a radiation are masked, and added and averaged into reference data. The ratio between the reference data and the corrective image data is generated as sensitivity correcting data. Desired radiation image information is then read from the stimulable phosphor sheet, corrected by the sensitivity correcting data, and outputted to an external image processing apparatus.

31 Claims, 8 Drawing Sheets

RADIATION IMAGE INFORMATION READING APPARATUS WITH RADIATION CONVERSION PANEL, AND METHOD OF CORRECTING SENSITIVITY OF RADIATION CONVERSION PANEL

BACKGROUND OF THE INVENTION

1. Field of the Invention

The present invention relates to a radiation image information reading apparatus for reading radiation image information from a radiation conversion panel that is irradiated with a radiation, and a method of correcting the sensitivity of a radiation conversion panel.

2. Description of the Related Art

There is known a radiation image information recording and reading system which employs a stimulable phosphor which, when exposed to an applied radiation (X-rays, α-rays, β-rays, γ-rays, electron beams, ultraviolet radiation, or the like), stores a part of the energy of the radiation, and, when subsequently exposed to applied stimulating light such as visible light, emits light in proportion to the intensity of the stored energy of the radiation. In the radiation image information recording and reading system, the radiation image information of a subject such as a human body or the like is temporarily recorded in a radiation conversion panel having a stimulable phosphor sheet which comprises a stimulable phosphor layer in the form of a sheet, and then stimulating light such as a laser beam is applied to the radiation conversion panel to cause the radiation conversion panel to emit light representing the recorded radiation image information. The emitted light is photoelectrically read to produce an electric image signal. Based on the image signal, the radiation image information of the subject is outputted as a visible image on a recording medium such as a photographic photosensitive medium or the like or a display unit such as a CRT (Cathode Ray Tube) or the like. For details of the radiation image information recording and reading system, reference should be made to Japanese laid-open patent publication No. 55-12429.

The radiation conversion panel which is used in the radiation image information recording and reading system may comprise a scintillator for converting the energy of an applied radiation into visible light without temporarily storing the energy, rather than a stimulable phosphor sheet. Alternatively, the radiation conversion panel may comprise a solid-state radiation detector such as a thin-film transistor for converting the energy of an applied radiation directly into an electric signal.

The radiation conversion panels have their sensitivity lowered with the time that has elapsed from the shipment from the factory, i.e., the time for which they have been used, the number of times that they have been irradiated with a radiation, i.e., the number of shots taken thereby, or the irradiation dose accumulated thereon. Particularly, the radiation is not applied uniformly over the entire surface of the radiation conversion panel, but the irradiation dose thereof differs between a central area of the radiation conversion panel where the subject to be imaged is located most frequently and a peripheral area of the radiation conversion panel where the subject to be imaged is located less frequently. Furthermore, if the radiation is applied to the radiation conversion panel through an irradiation field stop, then any sensitivity drop is reduced in the peripheral area of the radiation conversion panel.

When radiation image information is recorded on or read from a radiation conversion panel whose sensitivity is lowered, the radiation conversion panel may fail to provide desired radiation image information due to sensitivity irregularities.

SUMMARY OF THE INVENTION

It is a general object of the present invention to provide a radiation image information reading apparatus which employs a radiation conversion panel for producing a highly accurate radiation image by correcting irregularities due to a sensitivity drop of the radiation conversion panel, and a method of correcting the sensitivity of a radiation conversion panel.

A principal object of the present invention to provide a radiation image information reading apparatus which employs a radiation conversion panel having an increased service life by correcting irregularities due to a sensitivity drop thereof under conditions in which the radiation conversion panel is used, and a method of correcting the sensitivity of a radiation conversion panel.

Another object of the present invention to provide a radiation image information reading apparatus which employs a radiation conversion panel that is capable of correcting a sensitivity drop caused by the elapse of a time after the radiation conversion panel has started to be used, and a method of correcting the sensitivity of a radiation conversion panel.

Still another object of the present invention to provide a radiation image information reading apparatus which employs a radiation conversion panel that is capable of correcting a sensitivity drop caused by the application of a radiation to the radiation conversion panel, and a method of correcting the sensitivity of a radiation conversion panel.

According to the present invention, a radiation conversion panel is uniformly irradiated with a radiation at a certain time, and based on radiation image information produced by then reading the radiation conversion panel thus irradiated, sensitivity correcting data for correcting a sensitivity drop of the radiation conversion panel are calculated and stored in a corrective data memory. When desired radiation image information is read from the radiation conversion panel, the read radiation image information is corrected with the sensitivity correcting data read from the corrective data memory, thus providing highly accurate radiation image information from which irregularities due to the sensitivity drop have been removed.

The sensitivity correcting data can be calculated as follows: Reference data are set from image data of the radiation image information obtained by reading the radiation conversion panel uniformly irradiated with the radiation, and the sensitivity correcting data are calculated as a difference or ratio between the reference data and the image data.

Alternatively, the reference data may be calculated as average data of the image data or calculated from cumulative frequencies of the image data. If the reference data are produced by smoothing the image data, then a high-frequency component is removed from the reference data, and hence sensitivity correcting data free of the effect of noise can be obtained. The sensitivity correcting data thus produced should preferably be compressed and stored as small amount of data in the corrective data memory, and expanded for use when the radiation image information is to be corrected therewith.

Further alternatively, the reference data may be preset using a reference radiation conversion panel, and may be read for calculating sensitivity correcting data. In this case, a plurality of sensitivity data may be set depending on usage conditions such as the time that has elapsed from the shipment of the radiation conversion panel from the factory, i.e., the time for which the radiation conversion panel has been used, the number of times that the radiation conversion panel has been irradiated with the radiation and/or an accumulated irradiation dose of the radiation applied to the radiation conversion panel, the temperature of the radiation conversion panel, etc., and one of the reference data which corresponds to actual parameters may be selected to calculate sensitivity correcting data.

Image data read from the radiation conversion panel may not necessarily be proportional to usage conditions such as the irradiation dose of the radiation and the temperature of the radiation conversion panel. Therefore, sensitivity correcting data may be calculated under these usage conditions, and the image data may be corrected using the sensitivity correcting data thus calculated.

The radiation conversion panel has its sensitivity lowered depending on the time that has elapsed from the shipment of the radiation conversion panel from the factory, i.e., the time for which the radiation conversion panel has been used, the number of times that the radiation conversion panel has been irradiated with the radiation, or an accumulated irradiation dose of the radiation applied to the radiation conversion panel. A sensitivity drop of the radiation conversion panel is determined using these parameters, and the sensitivity correcting data are updated based on the determined sensitivity drop. Then, the sensitivity of the radiation conversion panel is corrected at a suitable time using the updated sensitivity correcting data, for thereby producing highly accurately radiation image information continuously from the radiation conversion panel. If the determined sensitivity drop is indicated to the operator, then the sensitivity correcting data may be updated in advance based on the indicated sensitivity drop.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
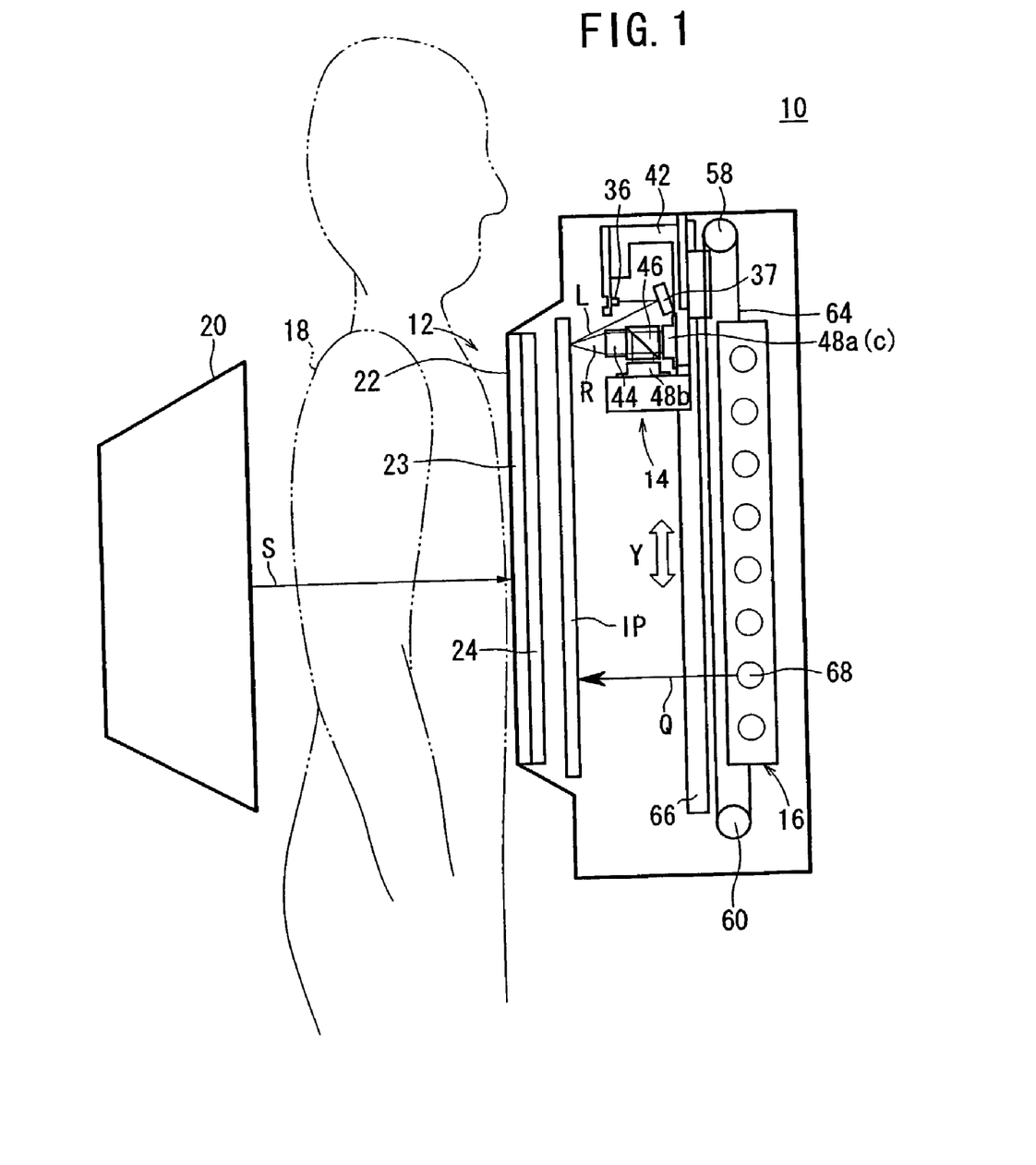
FIG. 1 is a schematic vertical cross-sectional view of a radiation image information recording and reading system according to an embodiment of the present invention.

FIG. 1 shows in schematic vertical cross-section a radiation image information recording and reading system 10 which incorporates a radiation image information reading apparatus with a radiation conversion panel and a method of correcting the sensitivity of a radiation conversion panel according to the present invention.

As shown in FIG. 1, the radiation image information recording and reading system 10 generally comprises a radiation recording unit 12 for temporarily recording the radiation image information of a subject 18 such as a human body or the like on a stimulable phosphor sheet IP (radiation conversion panel), a reading unit 14 for applying stimulating light L to the stimulable phosphor sheet IP and photoelectrically reading light R that is emitted from the stimulable phosphor sheet IP depending on the intensity of a radiation S applied to the subject 18, and an erasing light source 16 for discharging radiation energy that is left in the stimulable phosphor sheet IP.

The radiation recording unit 12 has a radiation source 20 for generating the radiation S and a radiation-permeable imaging base 22 for holding the subject 18 in position thereon. A phototimer 23 for accumulating the irradiation dose of the radiation S to control an irradiation time and a grid 24 for removing scattered rays are disposed behind the imaging base 22. The stimulable phosphor sheet IP is fixedly held in a given imaging position behind the grid 24.

The reading unit 14 is vertically movable along a guide rail 66 which extends vertically as indicated by the arrow Y. The reading unit 14 has a casing 42 held in movable engagement with the guide rail 66. The casing 42 is movable along the guide rail 66 in an auxiliary direction indicated by the arrow Y by a belt 64 which is connected to the casing 42 and trained around a drive pulley 58 and a driven pulley 60 that are positioned respectively at the upper and lower ends of the guide rail 66.

The reading unit 14 has a laser diode array 36 for outputting stimulating light L, disposed in an upper portion of the casing 42. The stimulating light L which is outputted as a linear beam from the laser diode array 36 is reflected by a mirror 37 fixed to the casing 42, and applied to the stimulable phosphor sheet IP in a main direction (horizontal direction) which is perpendicular to the auxiliary direction indicated by the arrow Y.

Line sensors 48a, 48b, 48c, such as CCDs, are disposed in a lower portion of the casing 42 for detecting light R which is emitted from the stimulable phosphor sheet IP in response to the stimulating light L, through a condenser lens array 44 and a prism 46, and photoelectrically converting the detected light R into an electric signal. The prism 46 serves to divide the light R into a beam to be applied to the line sensors 48a, 48c that are mounted on a vertical side panel of the casing 42 and a beam to be applied to the line sensor 48b that is mounted on a bottom panel of the casing 42. Each of the line sensors 48a, 48b, 48c comprises an array of photoelectric transducers arranged in the main direction (horizontal direction). The line sensors 48a, 48b, 48c may not necessarily be provided as three line sensors. The line sensors 48a, 48b, 48c are combined with filters (not shown) for passing the light R emitted from the stimulable phosphor sheet IP and blocking extraneous light including the stimulating light L.

The erasing light source 16 is positioned across the reading unit 14 from the stimulable phosphor sheet IP. The erasing light source 16 comprises a plurality of fluorescent lamps 68 for applying erasing light Q to the stimulable phosphor sheet IP to discharge radiation energy remaining in the stimulable phosphor sheet IP.

Figure 2:
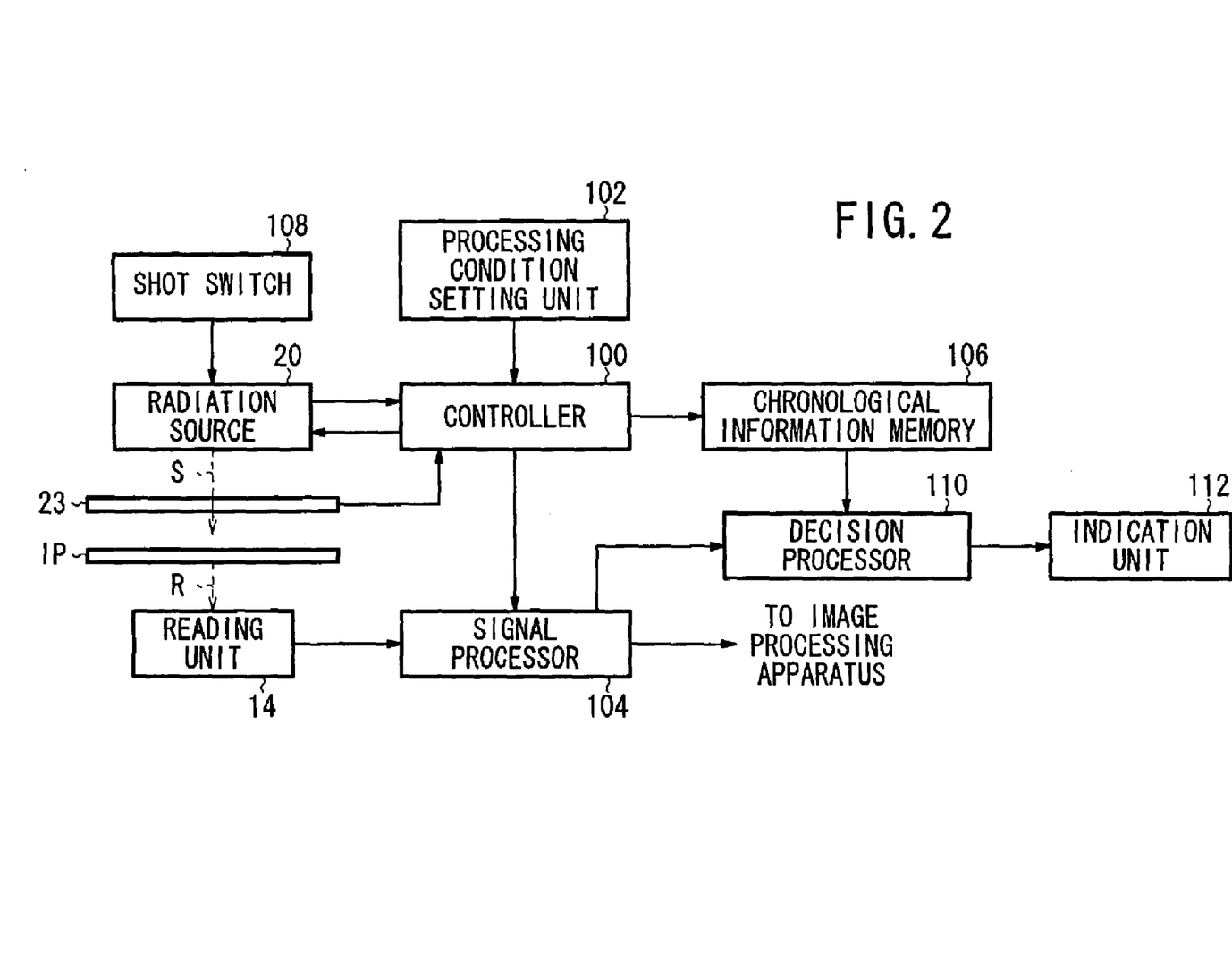
FIG. 2 is a block diagram of a control circuit in the radiation image information recording and reading system according to the embodiment of the present invention.

FIG. 2 shows in block form a control circuit in the radiation image information recording and reading system 10.

As shown in FIG. 2, the control circuit includes a controller 100 including a CPU (Central Processing Unit) for controlling the radiation image information recording and reading system 10 in its entirety. The control circuit also includes a processing condition setting unit 102, the radiation source 20, the phototimer 23, a signal processor 104, and a chronological information memory 106, all connected to the controller 100.

The processing condition setting unit 102 sets various data such as an irradiation dose of the radiation S to be applied from the radiation source 20 to the subject 18, an instruction for performing a process of generating sensitivity correcting data for the stimulable phosphor sheet IP, and a date and time when the stimulable phosphor sheet IP has started to be used, for example.

A shot switch 108 which is operable by the operator of the radiation image information recording and reading system 10 is connected to the radiation source 20. In response to a shot signal that is supplied from the shot switch 108 when the shot switch 108 is turned on by the operator, the radiation source 20 emits the radiation S and applies the radiation S to the stimulable phosphor sheet IP. The shot signal generated by the shot switch 108 is supplied through the radiation source 20 to the controller 100 in order to record the number of shots taken by the stimulable phosphor sheet IP.

The phototimer 23 accumulates the irradiation dose of the radiation S applied from the radiation source 20, and outputs a signal representing the accumulated irradiation dose to the controller 100. The controller 100 compares the accumulated irradiation dose from the phototimer 23 with an irradiation dose that is set by the processing condition setting unit 102, and outputs an inhibit signal for inhibiting the radiation S from being emitted to the radiation source 20 when the compared irradiation doses agree with each other.

The signal processor 104 performs various signal processing processes, including a process of correcting a sensitivity drop of the stimulable phosphor sheet IP, on the radiation image information read from the stimulable phosphor sheet IP by the reading unit 14, and outputs the processed radiation image information to an external image processing apparatus (not shown).

The chronological information memory 106 stores various items of chronological information such as the date and time when the stimulable phosphor sheet IP has started to be used, which date and time has been set by the processing condition setting unit 102, the date and time when a radiation drop of the stimulable phosphor sheet IP has previously been corrected, the number of shots of the radiation S which have been accumulated based on the shot signals generated so far by the shot switch 108, and the accumulated irradiation dose of the radiation S which has been accumulated so far by the phototimer 23, for example.

The chronological information memory 106 is connected to a decision processor 110. The decision processor 110 determines whether sensitivity correcting data are to be updated or not based on the chronological information from the chronological information memory 106, or determines how much the stimulable phosphor sheet IP has been damaged based on the sensitivity correcting data for the stimulable phosphor sheet IP which have been calculated by the signal processor 104. The determined results produced by the decision processor 110 are supplied to an indication unit 112 having a display unit, a speaker, etc.

Figure 3:
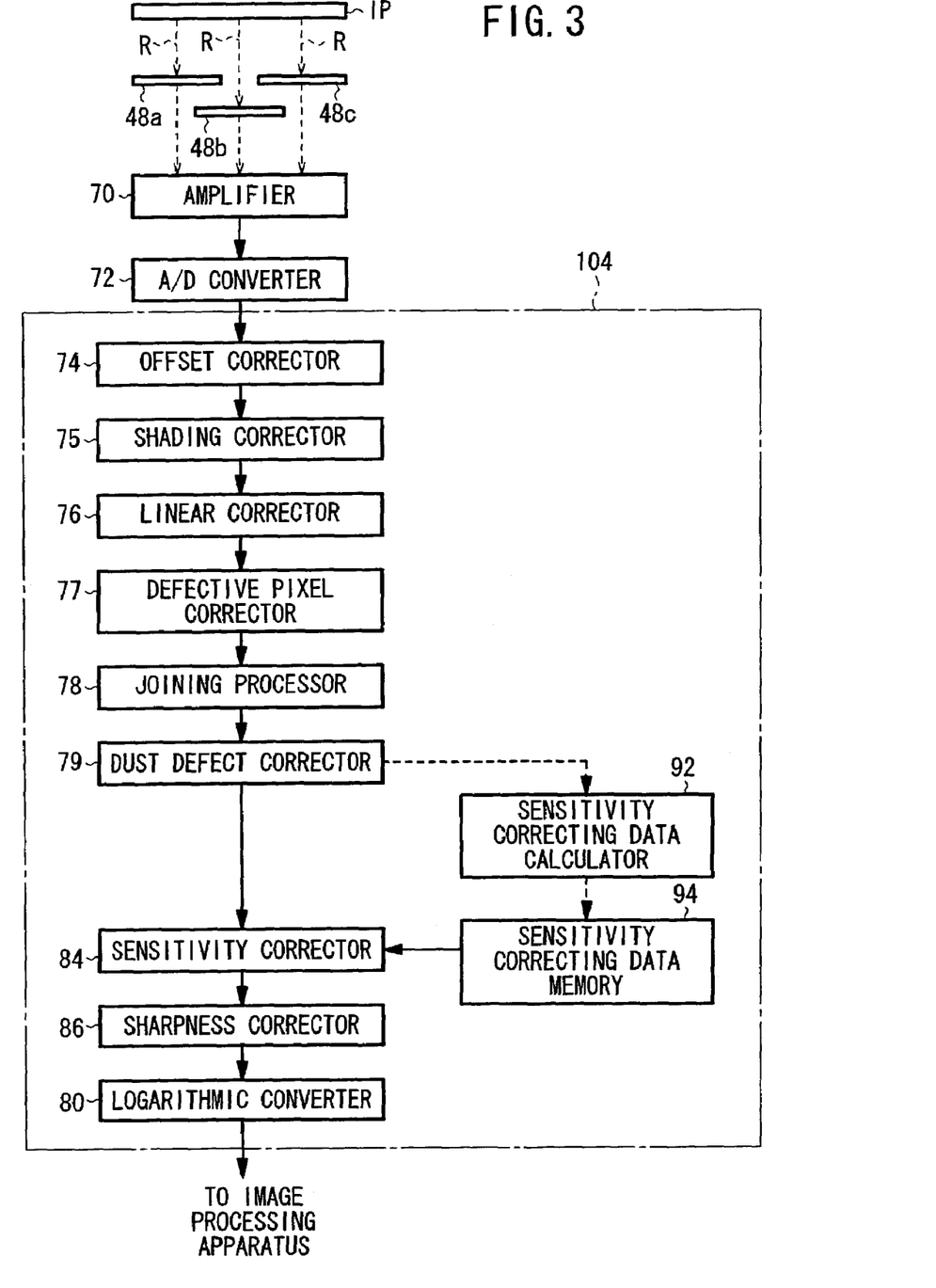
FIG. 3 is a block diagram of a reading unit and a signal processor in the control circuit shown in FIG. 2.

FIG. 3 shows in block form the reading unit 14 and the signal processor 104 in the control circuit shown in FIG. 2.

As shown in FIG. 3, the reading unit 14 has a processing circuit including an amplifier 70 for amplifying an electric signal produced by the line sensors 48a through 48c, and an A/D (Analog-to-Digital) converter 72 for converting the amplified electric signal into a digital image signal. The signal processor 104 comprises an offset corrector 74 for correcting offsets (dark levels and light leakages) of the line sensors 48a through 48c, a shading corrector 75 for correcting a shading due to sensitivity variations of the line sensors 48a through 48c, an amount-of-light distribution of the stimulating light L emitted from the laser diode array 36, and irregular light-converging characteristics of the condenser lens array 44, a linear corrector 76 for correcting the nonlinearity of the electric signal produced by the line sensors 48a through 48c to turn the signal into a linear signal, a defective pixel corrector 77 for correcting defective pixels of the photoelectric transducers of the line sensors 48a through 48c, a joining processor 78 for adjusting signals from joints between the line sensors 48a through 48c, a dust defect corrector 79 for correcting the effect of dust attached to the stimulable phosphor sheet IP, etc., a sensitivity corrector 84 for correcting a sensitivity drop of the image data according to sensitivity correcting data for correcting a sensitivity drop of the stimulable phosphor sheet IP, a sharpness corrector 86b for correcting the sharpness of the sensitivity-corrected image data in the main and auxiliary directions, and a logarithmic converter 80 for converting the sharpness-corrected image data into logarithmic image data and outputting the logarithmic image data to the external image processing apparatus.

The signal processor 104 also has a sensitivity correcting data calculator 92 (reference data setting unit) for calculating sensitivity correcting data to be supplied to the sensitivity corrector 84, the sensitivity correcting data calculator 92 being connected to the dust defect corrector 79. The sensitivity correcting data calculated by the sensitivity correcting data calculator 92 are stored in a sensitivity correcting data memory 94 which is connected to the sensitivity corrector 84. The sensitivity correcting data comprise data for correcting a sensitivity drop of the stimulable phosphor sheet IP. A sensitivity drop of the stimulable phosphor sheet IP occurs due to the time that has elapsed from the shipment of the stimulable phosphor sheet IP from the factory, i.e., the time for which the stimulable phosphor sheet IP has been used, an accumulated irradiation dose of the radiation applied to the stimulable phosphor sheet IP, etc. The sensitivity correcting data for correcting a sensitivity drop of the stimulable phosphor sheet IP are primarily made up of a slightly changing low-frequency component. According to the present embodiment, the sensitivity correcting data are compressed and stored as smaller sensitivity correcting data in the sensitivity correcting data memory 94.

The radiation image information recording and reading system 10 is basically constructed as described above. Operation and advantages of the radiation image information recording and reading system 10 will be described below.

First, a basic mode of operation of the radiation image information recording and reading system 10 will be described below.

Using the processing condition setting unit 102, the operator sets an irradiation dose of the radiation S depending on the age of the subject 18, an imaging area of the subject 18, etc. Thereafter, the operator positions the subject 18 in a predetermined location in the radiation recording unit 12, and operates the shot switch 108 to energize the radiation source 20 to apply the radiation S from the radiation source 20 to the subject 18. The radiation S that has passed through the subject 18 is transmitted through the phototimer 23 and the grid 24, and reaches the stimulable phosphor sheet IP where the radiation S records the radiation image information of the subject 18. While the stimulable phosphor sheet IP is being irradiated with the radiation S, the phototimer 23 accumulates the irradiation dose of the radiation S and outputs the accumulated irradiation dose to the controller 100, which compares the accumulated irradiation dose with the preset irradiation dose. When the accumulated irradiation dose agrees with the preset irradiation dose, the controller 100 outputs an inhibit signal to the radiation source 20 to inhibit the radiation source 20 from emitting the radiation S.

The controller 100 accumulates the number of shots based on the shot signal generated by the shot switch 108, and records the accumulated number of shots in the chronological information memory 106. The controller 100 also records the irradiation dose of the radiation S which is set by the processing condition setting unit 102, the accumulated irradiation dose of the radiation S which is produced by the phototimer 23, etc. in the chronological information memory 106.

After the recording of the radiation image information on the stimulable phosphor sheet IP is completed, the reading unit 14 is moved along the guide rail 66 in the direction indicated by the arrow Y to read the recorded radiation image information from the stimulable phosphor sheet IP. Stimulating light L outputted from the laser diode array 36 is reflected by the mirror 37 and applied to the stimulable phosphor sheet IP while being deflected in the main direction (horizontal direction). In response to the stimulating light L, the stimulable phosphor sheet IP emits light R representing the radiation image information stored therein. The emitted light R is applied through the condenser lens array 44 and the prism 46 to the line sensors 48a through 48c, which convert the light R into an electric signal. At this time, the radiation image information recorded on the stimulable phosphor sheet IP is two-dimensionally read by the line sensors 48a through 48c which move in the auxiliary direction, i.e., the direction indicated by the arrow Y.

When the process of reading the radiation image information from the stimulable phosphor sheet IP is finished, the erasing light source 16 is energized to apply erasing light Q from the fluorescent lamps 68 to the entire surface of the stimulable phosphor sheet IP, thereby removing residual radiation energy therefrom. Then, the stimulable phosphor sheet IP will be used to record next radiation image information.

After the radiation S is repeatedly applied to the stimulable phosphor sheet IP, the stimulable phosphor contained in the stimulable phosphor sheet IP has its sensitivity lowered depending on the accumulated irradiation dose. The sensitivity of the stimulable phosphor sheet IP also depends on the time that has elapsed from the shipment from the factory. Since the dose of the radiation S applied to the stimulable phosphor sheet IP is affected by the subject 18 and an irradiation field stop that is used in combination therewith, the sensitivity drop varies depending on the location on the stimulable phosphor sheet IP. Therefore, the radiation image information read from the stimulable phosphor sheet IP tends to suffer irregularities on account of those sensitivity drop variations. Consequently, it is necessary to generate sensitivity correcting data for correcting a sensitivity drop of the stimulable phosphor sheet IP, and correct the radiation image information using the sensitivity correcting data.

Figure 4:
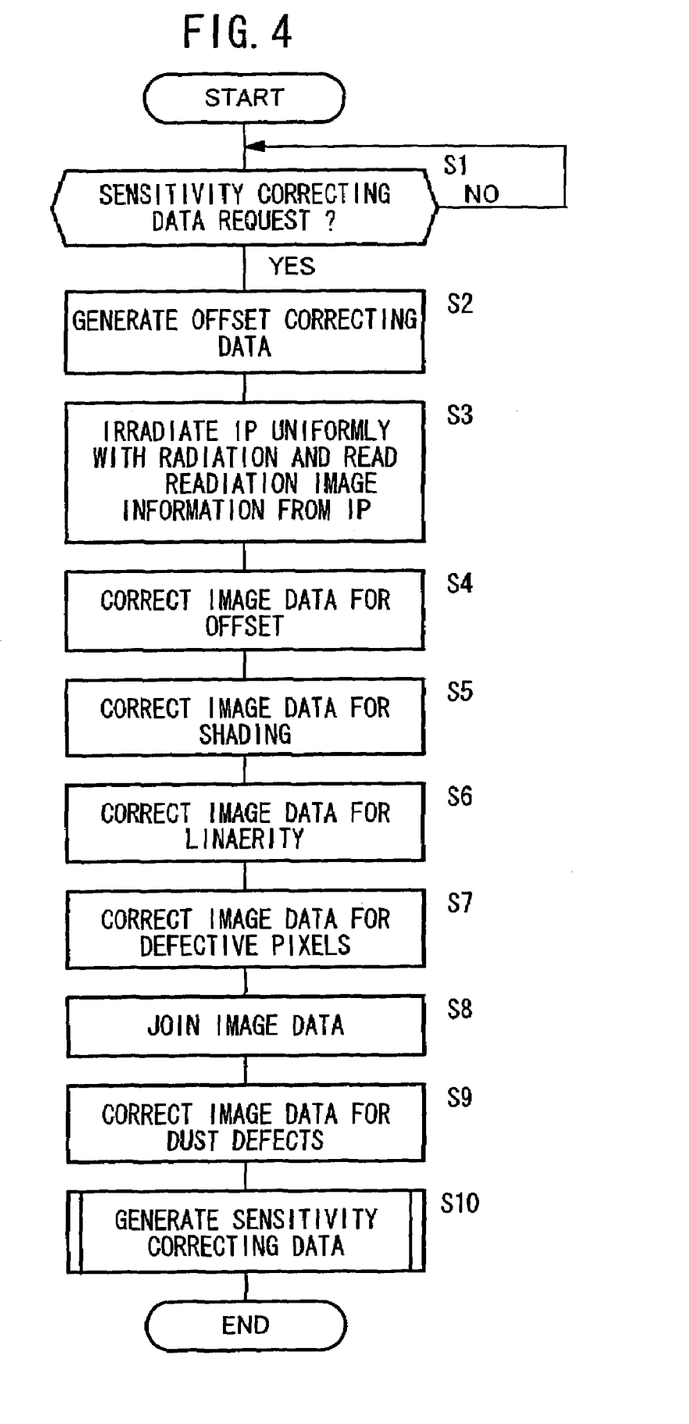
FIG. 4 is a flowchart of a sequence of generating sensitivity correcting data in the radiation image information recording and reading system according to the embodiment of the present invention.
Figure 5:
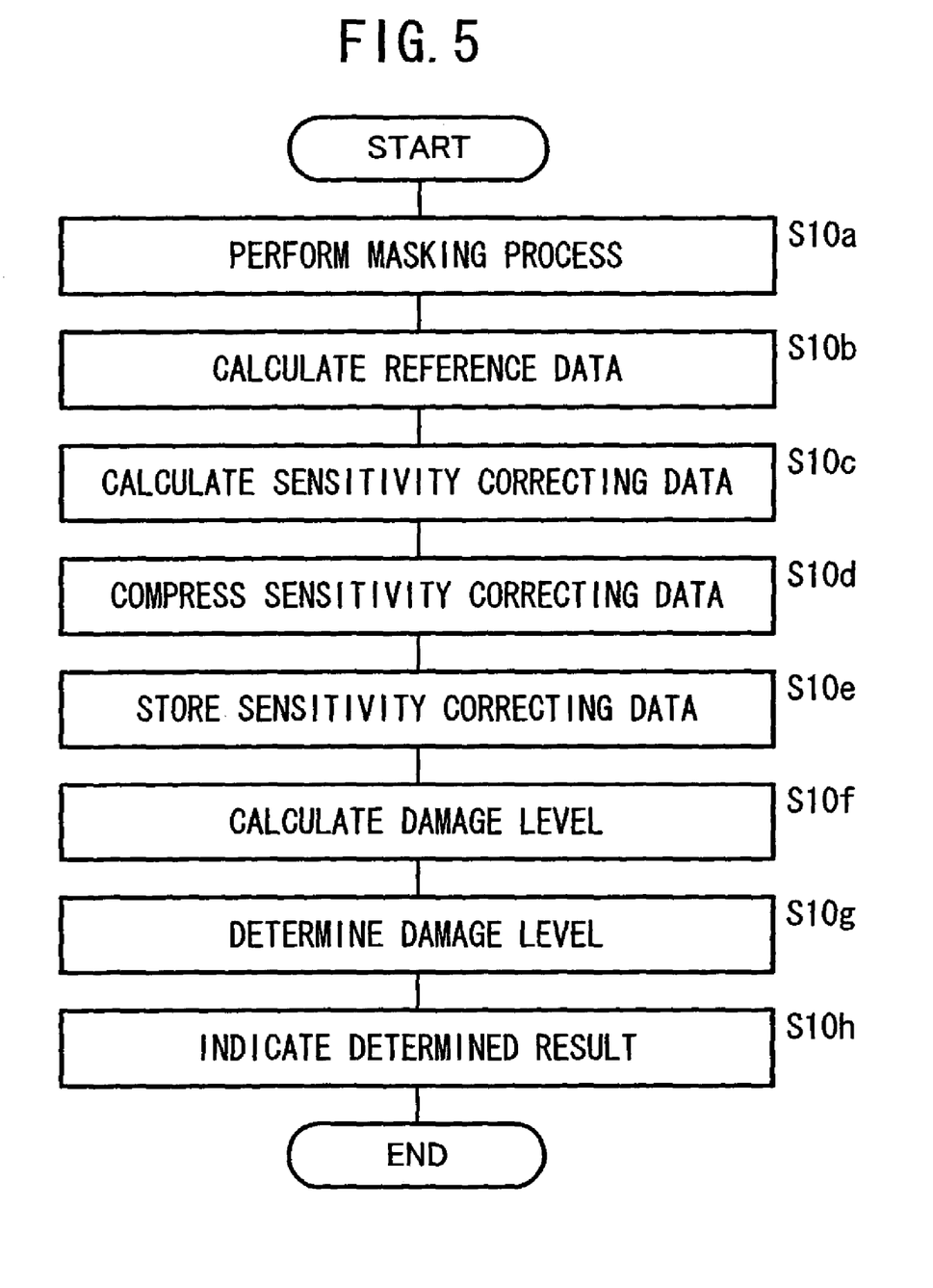
FIG. 5 is a flowchart of a detailed process of the sequence of generating sensitivity correcting data shown in FIG. 4.
Figure 6:
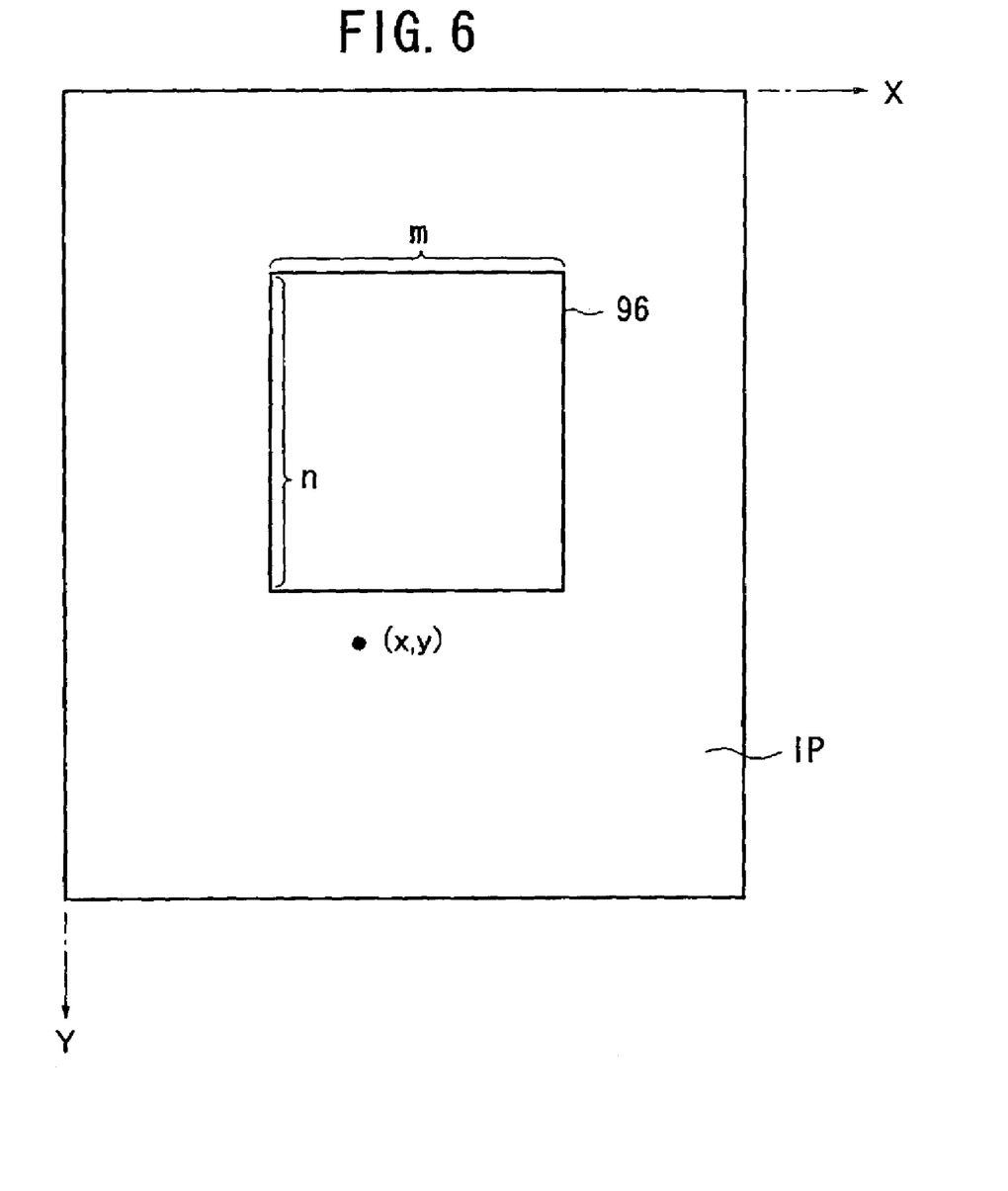
FIG. 6 is a diagram illustrative of a process of calculating a reference value for generating sensitivity correcting data.

A process of generating sensitivity correcting data will be described below with reference to FIGS. 4 and 5. It is assumed that, as shown in FIG. 6, the stimulable phosphor sheet IP is divided into image data in the main and auxiliary directions indicated by the respective arrows X, Y by the photoelectric transducers of the line sensors 48a through 48c, each image data being represented by coordinates (x, y) in an XY coordinate system having coordinate axes represented by the arrows X, Y.

The decision processor 110 determines whether it is necessary to generate sensitivity correcting data or not based on the chronological information from the chronological information memory 106. If the decision processor 110 decides that it is necessary to generate sensitivity correcting data, then the decision processor 110 operates the indication unit 112 to instruct the operator to generate sensitivity correcting data in step S1 shown in FIG. 4.

For example, the decision processor 110 monitors the date and time when the stimulable phosphor sheet IP has started to be used. After a predetermined period of time has elapsed since the stimulable phosphor sheet IP is used, because the stimulable phosphor sheet IP is possibly suffering a sensitivity drop, the decision processor 110 requests the operator to generate sensitivity correcting data via the indication unit 112. Alternatively, the date and time when the preceding sensitivity correcting data have been generated may be stored in the chronological information memory 106, and the decision processor 110 may request the operator to update the sensitivity correcting data after elapse of a given period of time from the date and time when the preceding sensitivity correcting data have been generated. The decision processor 110 may also request the operator to generate sensitivity correcting data when the radiation image information recording and reading system 10 starts to operate.

Furthermore, when the number of shots and/or the accumulated irradiation dose stored in the chronological information memory 106 exceeds a prescribed value, since the stimulable phosphor sheet IP has possibly been damaged by the radiation S, the decision processor 110 may request the operator to generate sensitivity correcting data through the indication unit 112.

If a minimum amount of erasing light Q which is required to erase residual radiation energy from the stimulable phosphor sheet IP is calculated from the maximum level of the radiation image information read by the reading unit 14 and the residual radiation energy is to be erased from the stimulable phosphor sheet IP by the calculated minimum amount of erasing light Q, then the accumulated amount of erasing light Q applied to the stimulable phosphor sheet IP may be stored in the chronological information memory 106. When the accumulated amount of erasing light Q reaches or exceeds a prescribed value, the decision processor 110 may decide that the stimulable phosphor sheet IP has been irradiated with at least a predetermined amount of radiation S and is damaged thereby, and may then request the operator to generate or update sensitivity correcting data through the indication unit 112.

The decision processor 110 may request not only the operator, typically an engineer who is daily handling the radiation image information recording and reading system 10, but also a maintenance worker for the radiation image information recording and reading system 10, to generate or update sensitivity correcting data through the indication unit 112. Rather than controlling the indication unit 112 to produce a visual or audio request for generating or updating sensitivity correcting data, the decision processor 110 may record log data as a basis for deciding on the generation or updating of sensitivity correcting data in the chronological information memory 106, and the maintenance worker may check the recorded log data upon periodic maintenance for generating or updating sensitivity correcting data.

If the generation of sensitivity correcting data is requested, then the laser diode array 36 of the reading unit 14 and the fluorescent lamps 68 of the erasing light source 16 are de-energized, and an electric signal from the line sensors 48a through 48c is detected through the amplifier 70 and the A/D converter 72. Dark level correcting data are then generated as offset correcting data from the electric signal in step S2. In the radiation image information recording and reading system 10, the stimulating light L tends to be partly applied to the line sensors 48a through 48c when the radiation image information is read from the stimulable phosphor sheet IP because the stimulating light L cannot be fully blocked by a filter or the like. To correct the effect of a leakage of the stimulating light L, light leakage correcting data have been generated at the time of shipment of the radiation image information recording and reading system 10, as offset correcting data in addition to the dark level correcting data.

Then, with the subject 18 being not placed in the radiation recording unit 12, the radiation source 20 applies the radiation S through the phototimer 23 and the grid 24 to the stimulable phosphor sheet IP uniformly over its surface. The reading unit 14 reads radiation image information from the stimulable phosphor sheet IP thus uniformly exposed to the radiation S in step S3. Specifically, the radiation image information recorded on the uniformly exposed stimulable phosphor sheet IP contains a slightly changing low-frequency component due to a sensitivity drop of the stimulable phosphor contained in the stimulable phosphor sheet IP.

Light R which is emitted from the stimulable phosphor sheet IP in response to the stimulating light L outputted from the laser diode array 36 is read by the line sensors 48a through 48c, and photoelectrically converted thereby into an electric signal. The electric signal is amplified by the amplifier 70, and then converted by the A/D converter 72 into a digital signal representing corrective image data.

The offset corrector 74 corrects offsets of the corrective image data using the offset correcting data generated in step S2 and the given light leakage correcting data in step S4.

Then, the shading corrector 75 corrects a shading of the offset-corrected corrective image data, which is caused by sensitivity variations of the line sensors 48a through 48c, an amount-of-light distribution of the stimulating light L emitted from the laser diode array 36, and irregular light-converging characteristics of the condenser lens array 44, using given shading correcting data in step S5.

Then, the linear corrector 76 corrects the nonlinearity of the shading-corrected corrective image data in step S6. The defective pixel corrector 77 corrects defective pixels of the nonlinearity-corrected corrective image data in step S7. The joining processor 78 performs a joining process on the corrective image data between the line sensors 48a through 48c in step S8. The dust defect corrector 79 corrects defects due to dust in the corrective image data in step S9. For example, the dust defect corrector 79 determines the cumulative frequencies of respective pixels of the corrective image data, and replaces those corrective image data whose cumulative frequencies are equal to or less than a predetermined ratio with the average value of surrounding corrective image data, thereby correcting the defects due to dust.

The corrective image data thus corrected are supplied to the sensitivity correcting data calculator 92, which generates sensitivity correcting data in step S10.

Specifically, as shown in FIG. 10, the sensitivity correcting data calculator 92 carries out a masking process on the corrective image data in step S10a. The masking process may be carried out as by adding and averaging a plurality of corrective image data around corrective image data in question. More specifically, if corrective image data in question are represented by D1(x,y), and the number of pixels around corrective image data in question is represented by j in the direction X and k in the direction Y, then masking image data D2(x,y) are determined by:

$$D2(x,y)=1/(j \cdot k) \cdot \Sigma\Sigma D1(x,y) \tag{1}$$

where $\Sigma\Sigma$ means the addition of corrective image data D1(x,y) over j pixels in the direction X and over k pixels in the direction Y. The values of j, k may be established in view of the amount of calculations involved in the masking process, the extent of a deviation of the reading position for the corrective image data D1(x,y) obtained from the stimulable phosphor sheet IP, the image quality of the corrective image data D1(x,y), etc. The masking process may be carried out as a process using a median filter or other filters.

With the masking process thus carried out, the effect of noise of a high-frequency component contained in the corrective image data D1(x,y) can be reduced. In addition, when the actual radiation image information is corrected using sensitivity correcting data which are generated based on the masking image data D2(x,y), the actual radiation image information is prevented from excessively corrected even if the corresponding sensitivity correcting data and the image data of the radiation image information are shifted out of positional alignment with each other.

The masking image data D2(x,y) in a given region which are made up of m×n pixels in a central area 96 (see FIG. 6) of the stimulable phosphor sheet IP are added and averaged, thus calculating reference data Qave expressed by:

$$Qave=1/(m \cdot n) \cdot \Sigma\Sigma D2(x,y) \tag{2}$$

in step S10b. In the above equation (2), $\Sigma\Sigma$ means the addition of making image data D2(x,y) in the central area 96 over m pixels in the direction X and over n pixels in the direction Y.

By thus determining the reference data Qave as the average of the making image data D2(x,y) in the central area 96, it is possible to correct the sensitivity in a peripheral area of the stimulable phosphor sheet IP where the sensitivity suffers a large drop, with respect to the central area 96 where the sensitivity suffers a small drop because the subject 18 is mainly positioned over the central area 96.

Figure 7:
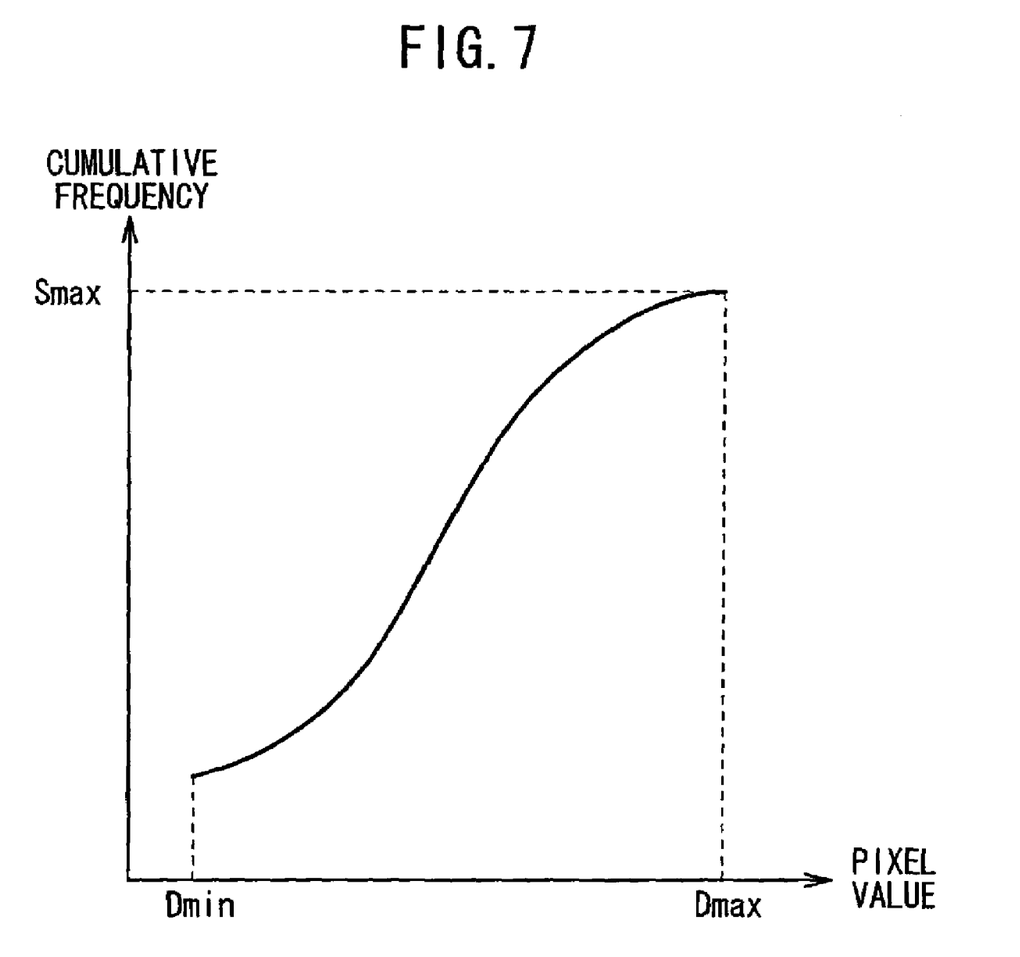
FIG. 7 is a diagram illustrative of another process of calculating a reference value for generating sensitivity correcting data.

The stimulable phosphor sheet IP may not necessarily have a large sensitivity drop in its peripheral area. If an irradiation field stop is used in combination with the stimulable phosphor sheet IP, or if the subject 18 is randomly positioned or has a randomly different size with respect to the stimulable phosphor sheet IP, then the stimulable phosphor sheet IP may have a different area where the sensitivity drops. For this reason, as shown in FIG. 7, cumulative frequencies of respective pixels of the masking image data D2(x,y) may be determined, and the pixel value Dmax when the cumulative frequencies are the maximum value Smax may be established as the reference data Qave. With the reference data Qave being thus established, masking image data $D2(x,y)$ obtained from an area of the stimulable phosphor sheet IP where damage due to the radiation W is minimum can be used as the reference data Qave.

Then, sensitivity correcting data $Qr(x,y)$ are determined as a ratio between the reference data Qave determined in step S10b and the corrective image data $D1(x,y)$ according to the following equation:

$$Qr(x,y)=Qave/D1(x,y) \quad (3)$$

in step S10c.

Since the sensitivity correcting data $Qr(x,y)$ thus determined comprises a low-frequency component, it can be compressed without causing a substantial reduction in the amount of information. The sensitivity correcting data calculator 92 then compresses the sensitivity correcting data $Qr(x,y)$ in step S10d, and stores the compressed sensitivity correcting data $Qr(x,y)$ as smaller data in the sensitivity correcting data memory 94 in step S10e. The sensitivity correcting data $Qr(x,y)$ may be compressed by reducing the amount of data by decimating the sensitivity correcting data $Qr(x,y)$.

The sensitivity correcting data $Qr(x,y)$ may be determined according to another process described below. Reference data Qlave are directly determined from the corrective image data $D1(x,y)$ according to the equation (2), and thereafter ratio data $Q2(x,y)$ between the reference data Qlave and the corrective image data $D1(x,y)$ is determined as follows:

$$Q2(x,y)=Qlave/D1(x,y) \quad (4)$$

Then, the ratio data $Q2(x,y)$ are subjected to a masking process to determine the sensitivity correcting data $Qr(x,y)$ as follows:

$$Qr(x,y)=1/(m \cdot n) \cdot \Sigma\Sigma Q2(x,y) \quad (5)$$

where $\Sigma\Sigma$ means the addition of the ratio data $Q2(x,y)$ over m pixels in the direction X and over n pixels in the direction Y.

The decision processor 110 calculates a damage level K of the stimulable phosphor sheet IP due to the radiation S using the corrective image data $D1(x,y)$ which have been obtained in generating the sensitivity correcting data $Qr(x,y)$ in step S10f. For example, the damage level K may be determined as the difference between the maximum pixel value Dmax and the minimum pixel value Dmin from the histogram of corrective image data $D1(x,y)$ shown in FIG. 7. The decision processor 110 then determines whether or not the damage level K is equal to or greater than a prescribed value in step S10g, and indicates the result through the indication unit 112 to the operator in step S10h. Based on the indicated result, the operator can judge whether the radiation image information recording and reading system 10 is to be used as it is or the stimulable phosphor sheet IP is to be replaced.

The damage level K may alternatively be determined as the minimum pixel value Dmin of the corrective image data $D1(x,y)$. In this case, the prescribed value to be compared with the damage level K should preferably be established depending on the dose of the radiation S that is applied to the stimulable phosphor sheet IP. The damage level K may not necessarily be calculated and indicated at the same time that the sensitivity correcting data $Qr(x,y)$ are generated, but may be calculated and indicated at a different time.

After the sensitivity correcting data $Qr(x,y)$ are thus generated, a process of reading the radiation image information from the stimulable phosphor sheet IP is carried out.

Figure 8:
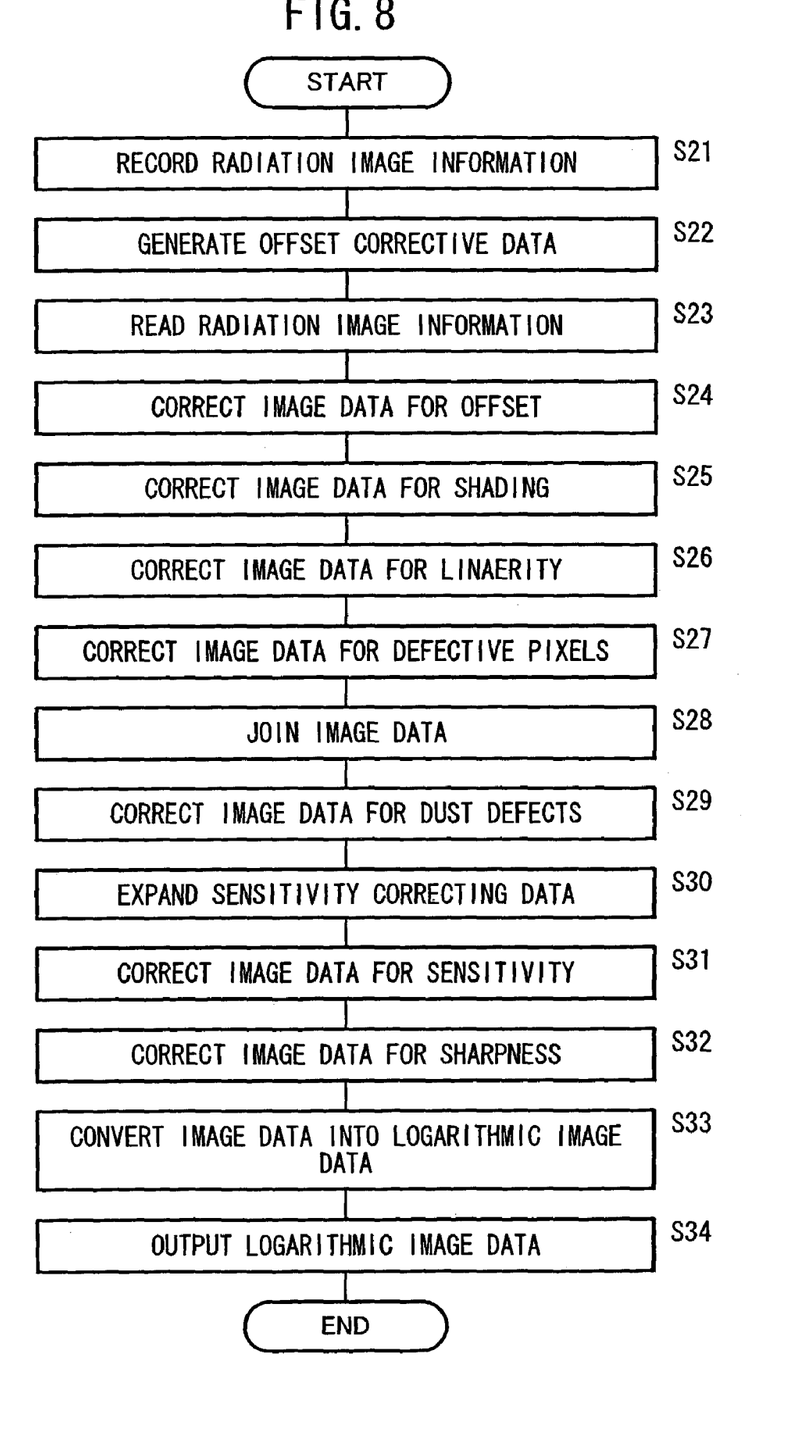
FIG. 8 is a flowchart of a correcting process using generated sensitivity correcting data.

The process of reading the radiation image information from the stimulable phosphor sheet IP will be described below with reference to FIG. 8.

The operator positions the subject 18 in a predetermined location in the radiation recording unit 12, and energizes the radiation source 20 to apply the radiation S from the radiation source 20 to the subject 18. The radiation S that has passed through the subject 18 is transmitted through the phototimer 23 and the grid 24, and reaches the stimulable phosphor sheet IP where the radiation S records the radiation image information of the subject 18 in step S21.

Prior to reading the recorded radiation image information from the stimulable phosphor sheet IP, dark level correcting data are generated as offset correcting data in the same manner as with step S2 described above in step S22. Since the dark level correcting data tend to vary depending on the temperature of the radiation image information recording and reading system 10, it is preferably to generate the dark level correcting data at periodic intervals or immediately prior to reading cycles.

Then, the reading unit 14 is energized to read the radiation image information recorded on the stimulable phosphor sheet IP in step S23. Image data $Dorg(x,y)$ based on the radiation image information read from the stimulable phosphor sheet IP are corrected for offsets by the offset corrector 74 based on the dark level correcting data generated in step S22 and given light leakage correcting data in step S24. Then, the offset-corrected image data $Doff(x,y)$ are then corrected for a shading by the shading corrector 75 in step S25, corrected for linearity by the linear corrector 76 in step S26, corrected for defective pixels by the defective pixel corrector 77 in step S27, joined between the line sensors 48a through 48c by the joining processor 78 in step S28, and corrected for dust defects by the dust defect corrector 79 in step S29. The image data are then supplied to the sensitivity corrector 84.

The sensitivity corrector 84 reads the sensitivity correcting data $Dr(x,y)$ compressed and stored in the sensitivity correcting data memory 94, and expands the sensitivity correcting data $Dr(x,y)$ into data in one-to-one correspondence to the image data $Dorg(x,y)$ in step S30.

Then, the sensitivity corrector 84 corrects the sensitivity of the image data $Dorg(x,y)$ corrected up to step S29, using the expanded sensitivity correcting data $Dr(x,y)$, and calculates the corrected image data $D(x,y)$ as follows:

$$D(x,y)=Dorg(x,y) \cdot Qr(x,y) \quad (6)$$

in step S31.

The sensitivity-corrected image data $D(x,y)$ are then corrected for sharpness in the main and auxiliary directions by the sharpness corrector 86 in step S32. Then, the sharpness-corrected image data $D(x,y)$ are converted by the logarithmic converter 80 into logarithmic image data in step S33. The logarithmic image data are thereafter outputted to the external image processing apparatus in step S34.

When the process of reading the radiation image information from the stimulable phosphor sheet IP is finished, the erasing light source 16 is energized to apply erasing light Q from the fluorescent lamps 68 to the entire surface of the stimulable phosphor sheet IP, thereby removing residual radiation energy therefrom. Then, the stimulable phosphor sheet IP will be used to record next radiation image information.

In the signal processor 104, the sensitivity-corrected image data are converted by the logarithmic converter 80 into logarithmic image data, which are outputted to the external image processing apparatus. However, after the image data corrected by the dust defect corrector 79 are converted by the logarithmic converter 80 into logarithmic image data, the logarithmic image data may be supplied to the sensitivity corrector 80 and corrected for sensitivity thereby, and the sensitivity-corrected image data may be outputted to the external image processing apparatus. In this modification, the sensitivity correcting data $Qr(x,y)$ are calculated as the difference between the reference data Qave and the corrective image data $D1(x,y)$, rather than according to the equation (3), and the sensitivity-corrected image data $D(x,y)$ are calculated as the sum of the image data $Dorg(x,y)$ and the sensitivity correcting data $Qr(x,y)$, rather than according to the equation (6).

In the above embodiment, the single stimulable phosphor sheet IP is fixed in position in the radiation image information recording and reading system 10. However, the principles of the present invention are also applicable to a system for recording radiation image information on a plurality of stimulable phosphor sheets IP that are successively fed to the radiation recording unit, where a sensitivity drop of each of the supplied stimulable phosphor sheets IP is corrected. In this case, the damage level of stimulable phosphor sheets IP varies depending on stimulable phosphor sheets IP. Therefore, it is preferable to generate sensitivity correcting data for the respective stimulable phosphor sheets IP, identify the stimulable phosphor sheets IP based on identification information such as bar codes or the like, and select corresponding sensitivity correcting data for the identified stimulable phosphor sheets IP to correct sensitivity irregularities thereof.

In a system where the stimulable phosphor sheet IP is fed and positioned in a given recording unit, if the stimulable phosphor sheet IP is not accurately positioned in the recording unit, then since image data read from the stimulable phosphor sheet IP and sensitivity correcting data are shifted out of positional alignment with each other, the sensitivity of the stimulable phosphor sheet IP cannot be corrected highly accurately. To prevent the above drawback, a marker, for example, is recorded as a reference position indicator on the stimulable phosphor sheet IP, and the stimulable phosphor sheet IP is corrected out of a positional misalignment based on the marker thereby to bring the image data and the sensitivity correcting data into accurate positional alignment with each other, so that the sensitivity of the stimulable phosphor sheet IP can be corrected highly accurately.

The sensitivity correcting data $Qr(x,y)$ may be generated as follows: The radiation S is applied uniformly to a plurality of stimulable phosphor sheets IP thereby to obtain a plurality of sets of corrective image data, which are then averaged into reference data Qave, and sensitivity correcting data $Qr(x,y)$ are generated from the reference data Qave.

Alternatively, the radiation S is applied uniformly to a stimulable phosphor sheet IP which has not been damaged by the radiation S or the like, and reference data Qave are generated from image data which have been produced from the stimulable phosphor sheet IP. Corrective image data $D1(x,y)$ are determined from a damaged stimulable phosphor sheet IP. Sensitivity correcting data $Qr(x,y)$ are generated from the reference data Qave and the corrective image data $D1(x,y)$.

The reference data Qave may be generated and saved when a reference stimulable phosphor sheet IP is fabricated or designed, and then read and used when sensitivity correcting data $Qr(x,y)$ are generated. In this case, it is preferable to prepare a plurality of reference data Qave depending on usage conditions such as the time that has elapsed from the shipment of the stimulable phosphor sheet IP from the factory, i.e., the time for which the stimulable phosphor sheet IP has been used, the number of times that the stimulable phosphor sheet IP has been irradiated with the radiation W, the irradiation dose, the type of the stimulable phosphor sheet IP, the temperature of the stimulable phosphor sheet IP, etc., and to select one of the prepared reference data Qave which corresponds to the actual usage conditions when reference correcting data $Qr(x,y)$ are to be generated.

If reference data are determined with respect to a reference irradiation dose, and reference data are calculated with respect to any desired irradiation dose, then sensitivity correcting data $Qr(x,y)$ can be determined highly accurately using reference data comprising a small amount of data, and accurate radiation image information can be obtained using the sensitivity correcting data $Qr(x,y)$. The same process applies to any of the other usage conditions.

Image data read from the stimulable phosphor sheet IP may not necessarily be proportional to usage conditions such as the irradiation dose of the radiation S and the temperature of the stimulable phosphor sheet IP. Therefore, sensitivity correcting data $Qr(x,y)$ may be calculated under these usage conditions, and the image data may be corrected using the sensitivity correcting data $Qr(x,y)$ thus calculated.

Inasmuch as the radiation image information reading apparatus or stimulable phosphor sheet IP expands and contracts depending on the temperature thereof, if the temperature at which the sensitivity correcting data $Qr(x,y)$ are generated for the stimulable phosphor sheet IP and the temperature at which desired radiation image information is read from the stimulable phosphor sheet IP are different from each other, the sensitivity correcting data $Qr(x,y)$ and the read radiation image information are brought out of desired positional alignment with each other, resulting in a failure to correct the image data properly. To avoid this shortcoming, a plurality of temperature-dependent sensitivity correcting data $Qr(x,y)$ may be generated using reference data, and one of the sensitivity correcting data $Qr(x,y)$ may be selected depending on the actual temperature or sensitivity correcting data $Qr(x,y)$ may be calculated and corrected by way of interpolation, for thereby obtaining radiation image information which is corrected highly accurately that is free from the effect of any unwanted positional data misalignment.

The radiation image information reading apparatus according to the present invention is applicable not only to correcting sensitivity irregularities caused by the application of a radiation to a stimulable phosphor sheet, but also to correcting sensitivity irregularities of a scintillator for converting a radiation into visible light and sensitivity irregularities of a thin-film transistor for converting a radiation directly into an electric signal.

Although a certain preferred embodiment of the present invention has been shown and described in detail, it should be understood that various changes and modifications may be made therein without departing from the scope of the appended claims.

What is claimed is:

1. A radiation image information reading apparatus for reading radiation image information from a radiation conversion panel irradiated with a radiation, comprising:
    a corrective data calculator for calculating sensitivity correcting data for correcting a sensitivity drop of said radiation conversion panel based on radiation image information obtained by reading said radiation conversion panel which has been irradiated with the radiation;

a corrective data memory for storing said sensitivity correcting data; and a sensitivity corrector for correcting the radiation image information read from said radiation conversion panel with said sensitivity correcting data;

wherein said corrective data calculator has a reference data setting unit for setting reference data with respect to image data of the radiation image information obtained by reading said radiation conversion panel which has been irradiated with the radiation, and said corrective data calculator calculates said sensitivity correcting data from said image data and said reference data.

2. A radiation image information reading apparatus according to claim 1, wherein said reference data setting unit sets average data of said image data as said reference data.

3. A radiation image information reading apparatus according to claim 1, wherein said reference data setting unit sets said reference data from cumulative frequencies of the respective image data.

4. A radiation image information reading apparatus according to claim 1, wherein said reference data setting unit sets said reference data from smoothed data produced by smoothing said image data.

5. A radiation image information reading apparatus according to claim 1, wherein said reference data setting unit determines and sets said reference data from said radiation conversion panel.

6. A radiation image information reading apparatus according to claim 5, wherein said reference data setting unit sets a plurality of reference data corresponding to usage conditions from said radiation conversion panel, and selects one of said reference data corresponding to actual usage conditions for generating said sensitivity correcting data.

7. A radiation image information reading apparatus according to claim 1, wherein said corrective data calculator calculates the sensitivity correcting data corresponding to usage conditions for said radiation conversion panel.

8. A radiation image information reading apparatus according to claim 1, further comprising:

a corrective data compressor for compressing said sensitivity correcting data and storing the compressed sensitivity correcting data in said corrective data memory.

9. A radiation image information reading apparatus according to claim 1, further comprising:

a sensitivity drop decision unit for determining the sensitivity drop of said radiation conversion panel based on a time for which said radiation conversion panel has been used.

10. A radiation image information reading apparatus according to claim 1, further comprising:

a sensitivity drop decision unit for determining the sensitivity drop of said radiation conversion panel based on the number of times that said radiation conversion panel has been irradiated with the radiation and/or the irradiation dose of the radiation applied to said radiation conversion panel.

11. A radiation image information reading apparatus according to claim 1, further comprising:

a sensitivity drop decision unit for determining the sensitivity drop of said radiation conversion panel; and an indication unit for indicating a determined result from said sensitivity drop decision unit.

12. The apparatus of claim 11, comprising a chronological information memory storing information related to radiation exposure information corresponding to the radiation conversion panel, the radiation exposure information being updated with each use of the radiation conversion panel, and said sensitivity drop decision unit determines the sensitivity drop based on the radiation exposure information.

13. The apparatus of claim 12, said chronological information memory further storing information relating to lapse of time from manufacture for said radiation conversion panel, and said sensitivity drop decision unit determines the sensitivity drop based on the lapse of time from manufacture.

14. The apparatus according to claim 1, wherein the sensitivity drop is determined from multiple pixels of the image information.

15. The apparatus according to claim 1, wherein the sensitivity drop varies over time, and said corrective data calculator automatically determines the sensitivity correction data to account for the variation.

16. The apparatus of claim 1, wherein the radiation conversion panel stores at least one of x-ray, $\alpha$-ray, $\beta$ ray, ultra violet, electron beam and $\gamma$ ray radiation.

17. The apparatus of claim 1, wherein the sensitivity correcting data for a two-dimensional radiation conversion panel are calculated.

18. The apparatus of claim 1, wherein the sensitivity corrector also corrects the radiation image information based partially on data that has been previously stored in addition to said sensitivity correcting data.

19. The apparatus of claim 1 wherein the reading apparatus includes a photosensor, and a shading corrector to take into account sensitivity variation in the photosensor.

20. A radiation image information reading apparatus according to claim 1, wherein said reference data are set based on said image data of an area in said radiation conversion panel, where sensitivity suffers a small drop.

21. A method of correcting the sensitivity of a radiation conversion panel in a radiation image information reading apparatus for reading radiation image information from the radiation conversion panel irradiated with a radiation, comprising the steps of:

applying the radiation to said radiation conversion panel;

setting reference data with respect to image data of the radiation image information obtained by reading said radiation conversion panel;

calculating sensitivity correcting data for correcting a sensitivity drop of said radiation conversion panel based on said image data and said reference data; and applying the radiation to said radiation conversion panel and correcting radiation image information obtained from said radiation conversion panel with said sensitivity correcting data.

22. A method according to claim 21, wherein said reference data are calculated from average data of said image data obtained by applying the radiation uniformly to said radiation conversion panel.

23. A method according to claim 21, wherein said reference data are calculated from cumulative frequencies of said image data obtained by applying the radiation uniformly to said radiation conversion panel.

24. A method according to claim 21, wherein said reference data are calculated from smoothed data produced by smoothing said image data obtained by applying the radiation uniformly to said radiation conversion panel.

25. A method according to claim 21, wherein said reference data are set from said radiation conversion panel.

26. A method according to claim 25, wherein said reference data are set as a plurality of reference data corresponding to usage conditions from said radiation conversion panel, and one of said reference data corresponding to actual usage conditions is selected for generating said sensitivity correcting data.

27. A method according to claim 21, wherein said reference data are calculated so as to correspond to usage conditions for said radiation conversion panel.

28. A method according to claim 21, further comprising the steps of:
compressing and holding the calculated sensitivity correcting data; and
expanding the compressed sensitivity correcting data;
wherein said radiation image information is corrected using the expanded sensitivity correcting data.

29. A method according to claim 21,
wherein said reference data are set based on said image data of an area in said radiation conversion panel, where the sensitivity suffers a small drop.

30. A radiation image information reading apparatus for reading radiation image information from a radiation conversion panel irradiated with a radiation, comprising:

a corrective data calculator for calculating sensitivity correcting data for correcting a sensitivity drop of said radiation conversion panel based on radiation image information obtained by reading said radiation conversion panel which has been irradiated with the radiation;

a corrective data memory for storing said sensitivity correcting data; and a sensitivity corrector for correcting the radiation image information read from said radiation conversion panel with said sensitivity correcting data.

31. A radiation image information reading apparatus according to claim 30,
wherein reference data are set based on image data of an area in said radiation conversion panel, where sensitivity suffers a small drop.

* * * * *